United States Patent [19]

Palfray

[11] Patent Number: 5,065,770

[45] Date of Patent: Nov. 19, 1991

[54] APPARATUS FOR PLOTTING THE CONFIGURATION OF A LOWER LIMB OF THE HUMAN BODY WITH A VIEW TO PRODUCING AN ORTHESIS FOR PARAPLEGIC

[75] Inventor: Michel Palfray, Seurre, France

[73] Assignee: Establissements Proteor, France

[21] Appl. No.: 424,535

[22] Filed: Oct. 20, 1989

[30] Foreign Application Priority Data

Oct. 21, 1988 [FR] France ............................ 88 13841

[51] Int. Cl.$^5$ .............................................. A61B 5/10
[52] U.S. Cl. .................................. 128/774; 128/80 F; 128/89 R
[58] Field of Search ................. 128/80 R, 80 B, 80 F, 128/85-87 R, 88, 89 R, 774, 779, 781

[56] References Cited

U.S. PATENT DOCUMENTS

| | | | |
|---|---|---|---|
| 158,893 | 1/1875 | Bissell | 128/88 |
| 158,894 | 1/1875 | Bissell | 128/88 |
| 1,517,915 | 12/1924 | Masland | 128/88 |
| 3,651,803 | 3/1972 | Bimler | 128/88 |
| 3,844,279 | 10/1974 | Konvalin | 128/80 F |
| 4,336,796 | 6/1982 | Andrews et al. | 128/88 |

FOREIGN PATENT DOCUMENTS 2403776 4/1979 France .
1499807 2/1978 United Kingdom .

Primary Examiner—David Shay
Attorney, Agent, or Firm—Scully, Scott, Murphy & Presser

[57] ABSTRACT

The invention relates to an apparatus for plotting the conformation of a lower limb of the human body, this apparatus comprising two sets of two longitudinal uprights, or splints (1), the splints of one and the same set being mutually articulated by an orthesis articulation (2) of a known type, and a plurality of cross-pieces forming braces (8, 10, 12) which transversely connect the splints (1) at various intervals. According to the invention, the spints (1) are deforable in such a way that they can be applied tighlty agains the limb in question in order to match the profile thereof, and the crosspieces (8, 10, 12) connecting these splints have an adjustable transverse dimension, so as to be able to regulate the spacing of the splints.

8 Claims, 1 Drawing Sheet

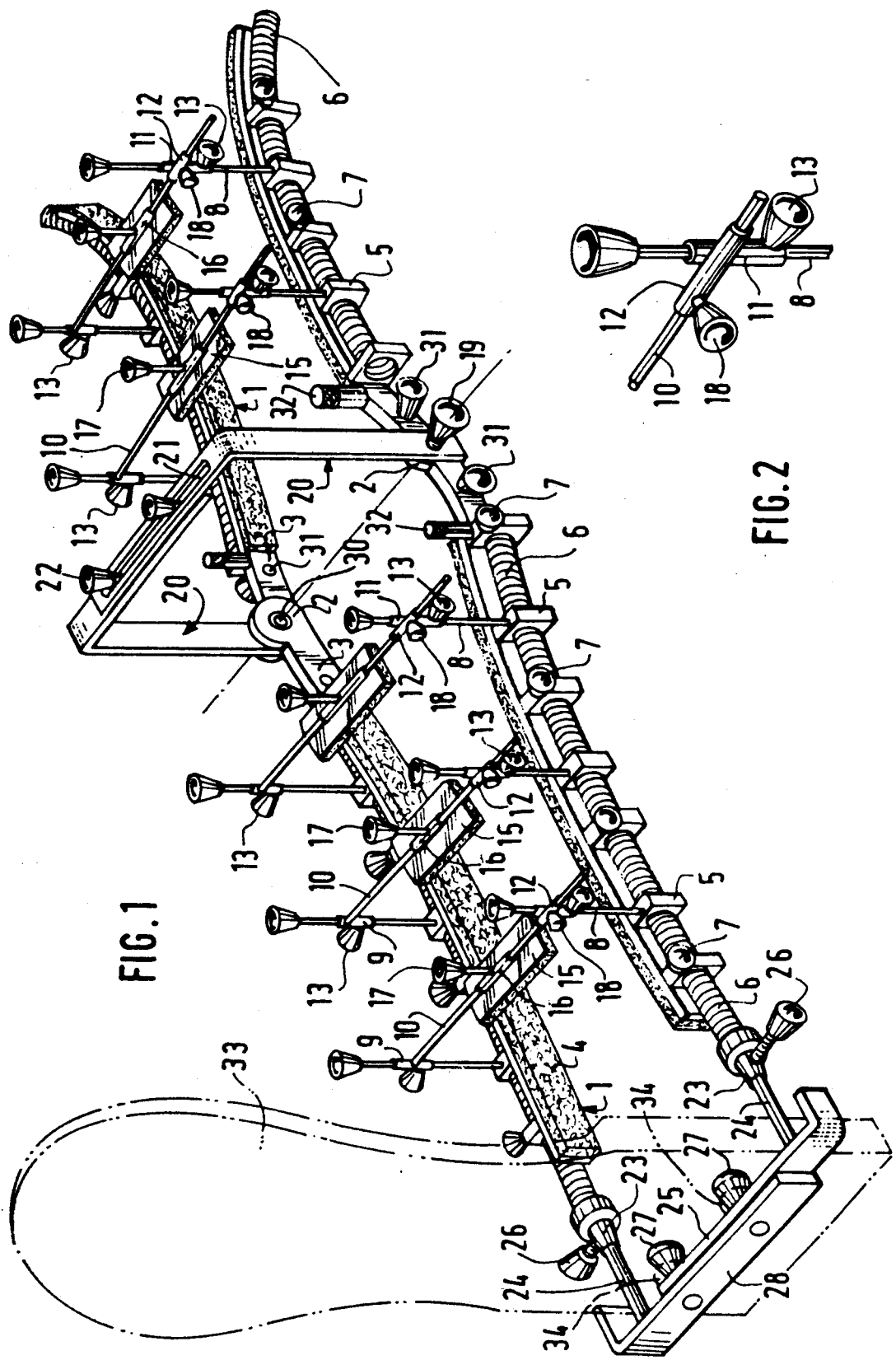

APPARATUS FOR PLOTTING THE CONFIGURATION OF A LOWER LIMB OF THE HUMAN BODY WITH A VIEW TO PRODUCING AN ORTHESIS FOR PARAPLEGIC

BACKGROUND OF THE INVENTION

1. Field of the Invention

The present invention relates to an apparatus for plotting the configuration of a lower limb of the human body. The invention also relates to the use of this apparatus for producing an orthesis for a paraplegic.

2. Discussion of the Prior Art

It is known that such ortheses comprise two sets of longitudinal splints or props which are arranged laterally on each side of the limb to be fitted and are connected transversely by braces, each set of splints being equipped with an articulation at the level of the knee.

In order to manufacture these ortheses by shaping them to the limb of the patient, a plaster cast of this limb is normally used or a tracing of the outline of this limb is made on a sheet of paper, and from these an orthesis is made which is tested on the patient in the use position, that is to say standing.

The necessary modifications are made to this first orthesis and a second test fitting is then carried out, followed by new corrections, before obtaining the final orthesis.

These operations are long and fastidious, since the splints, the braces and the articulations of the orthesis are normally of steel, aluminum or thermoplastic resin reinforced with carbon fibers.

SUMMARY OF THE INVENTION

One object of the present invention is, therefore, to provide an apparatus capable of plotting the conformation of a lower limb of a patient and of serving as a test orthesis capable of being adjusted on the patient in the standing position.

Another object of the invention is to provide such an apparatus forming a test orthesis which makes it possible to reduce the times for producing an orthesis for a lower limb and to limit the number of tests for the patient to be fitted.

To this end, the present invention provides an apparatus for plotting the conformation of a lower limb of the human body, this apparatus comprising two sets of two longitudinal uprights, or splints, the splints of one and the same set being mutually articulated by an orthesis articulation of a known type, and a plurality of crosspieces forming braces, which transversely connect the splints at various intervals, in which apparatus the splints are deformable in such a way that they can be applied tightly against the limb in question in order to match the profile thereof, and in that the crosspieces connecting these splints have an adjustable transverse dimension, so as to be able to regulate the spacing of the splints.

The crosspieces will comprise, for example, two first elements respectively integral with one of the splints connected by this crosspiece, these first elements projecting laterally in a manner substantially perpendicular to the associated splints on each side of the limb in question and, on the other hand, two second elements adjustable in position, respectively, relative to one of the first elements, these second elements being mutually coupled transversely in adjustable manner, relative to the splints, in such a way that one of them at least can be brought into contact with the limb in question and their assembly can be adapted to the spacing of the splints, locking means being provided in order to lock, in the assembled position, the said second elements relative to one another and relative to the first elements.

Advantageously, a crosspiece of adjustable width forming a brace will connect the two articulations of the apparatus and it will comprise, for example, two rigid corner irons of which two branches may be brought into contact with each other in an adjustable position and be locked in this position by a locking means. One of the branches will comprise, for example, a longitudinal cut-out, while the other branch will comprise at least one tapping facing this cutout, the locking means then consisting of a simple screw which will pass through the cut-out and will be screwed into the said tapping.

The splints may consist of deformable metallic strips called clinquants which can be curved as desired to match the shape of the limb in question. These splints will preferably be integral with a deformable element such as a flexible tube arranged on the outer face of the metallic strip relative to the limb. It will be possible for this flexible tube to pass through an opening of corresponding diameter in a member fixed on the outer face of the metallic strip, and a locking means, such as a screw engaged in a tapping in this member, will allow the flexible tube to be made rigidly integral with the said member and, thus, the strip.

The inner face of this strip intended to come into contact with the limb may advantageously be covered with a flexible material such as a foam of plastic material, a felt etc . . . in order to avoid direct contact between the metal and the skin of the patient.

The first elements of the crosspieces may consist of rods integral with the splint. These rods may, for example, be screwed into a tapping in the members through which the flexible tube passes, in the case where the splint comprises one.

The second members may be mounted slidably on these first members and comprise, on the one hand, a rod arranged transversely above the limb and the splints and, on the other hand, a sheath in which this rod can be engaged. The means for locking these second members in position will comprise, for example, a screw engaged in a tapping in the sheath.

A plate may be mounted pivotably on the rod of one of the second members, which plate is adjustable in position and is intended to come into contact with the limb of the patient. For example, the said rod will be mounted slidably and pivotably in a sheath integral with this plate, and a screw engaged in a tapping in this sheath will allow this plate to be locked in position. The face of this plate intended to come into contact with the limb will advantageously be covered with a layer of a flexible material, such as a foam of plastic material, a felt or other.

A stirrup will advantageously be arranged at the lower end of the splints, the branches of which stirrup will be arranged in an adjustable manner in the extension of the splints and the base of which stirrup will have an adjustable width, so as to be able to adjust the stirrup to the foot of the patient. It may consist of two right-angle braces, of which one branch will be mounted slidably relative to the splints, with a means for locking in position, while the two other branches will be in mutual contact in order to form the base of the stirrup, one comprising, for example, a longitudinal cut-out and the other at least one tapping arranged facing this cut-out, so as to be able to assemble the said branches in adjustable position by means of a simple screw.

BRIEF DESCRIPTION OF THE DRAWINGS

Other characteristics and advantages of the invention will appear in the following description of an embodiment of the apparatus according to the invention, with reference to the attached drawings, in which:

FIG. 1 is a perspective view of the apparatus;

FIG. 2 is a detailed view, on a larger scale, illustrating the articulation system of the transverse crosspieces.

A DETAILED DESCRIPTION OF THE DRAWINGS

The apparatus shown in the drawings comprises two sets of two longitudinal props or splints 1. These splints of one and the same set are mounted pivotably relative to each other by means of an orthesis articulation 2, of a type known per se, comprising two branches 3 articulated about an axle 30 and rigidly integral, respectively, by means of screws 31, with one of the splints. This articulation comprises a locking system of a common type (not shown).

The splints 1 consist of a deformable metallic strip intended to be applied laterally against the limb of the patient, and they are covered, on their face intended to come into contact with the limb to be fitted, by a layer 4 of a flexible material. Fixed perpendicularly on their other face are rigid plates 5, in a central opening of which a flexible tube 6 is slidably mounted. Starting from their edge, the plates 5 are pierced with a tapping leading into the central opening of the plate and in which there is screwed a screw 7, which thus permits the flexible tube 6 to be made integral in any position with the various plates 5, and to thereby lock the associated splint in a position corresponding to the curvature of the limb to be fitted.

In a tapping formed in one edge of the plates, which is perpendicular to the splints, a rod 8 is screwed parallel to the associated splint. A sheath 9 is mounted slidably on a rod 8 integral with one of the splints, from which sheath 9 a rod 10 extends transversely in the direction of the other splint. A sheath 11 is mounted slidably on an associated rod 8 in a position corresponding to this other splint, from which sheath 11 there extends transversely a second sheath 12 in which the rod 10 is slidably mounted. Screws, such as 13, screwed into tappings passing through the sheaths 9 and 11 allow the latter to be locked on the rods 8 in a position corresponding to the contact of the rod 10 with the limb of the patient, that is to say in a position corresponding to the associated dimension of this limb. In order to avoid a direct contact between the rod 10 and the limb, a plate 15, integral with a sheath 16 in which the rod 10 is slidably mounted, can be mounted pivotably relative to this rod. A screw 17, engaged in a tapping passing through the sheath 16, allows the plate 15 to be locked in any position on the rod 10. The face of this plate intended to come into contact with the limb to be fitted will advantageously be covered by a layer of a flexible material.

A screw 18, screwed into a tapping passing through the sheath 12, allows the latter to be made integral with the rod 10 in any position and to thereby lock the rods 8 and, consequently, the splints 1 with a spacing corresponding to the transverse dimension of the limb to be fitted.

On one of the branches 3 of each articulation 2 there is fixed, by means of a screw 19, a branch of a rigid corner iron 20, of which the other branch, extending transversely above the splints 1, comes to bear against the corresponding branch of the associated corner iron on the other articulation. A longitudinal cut-out 21 is made in one of the branches in contact, while the other branch is pierced with at least one tapping facing this cut-out (two in the present case), so as to be able to join the two corner irons by means of screws such as 22.

A tubular element 23 is fixed at the end of the flexible tubes 6 corresponding to the foot of the patient. In these tubular elements, arranged following the axis of the flexible tubes, a cylindrical branch 24 of a corner iron is mounted slidably, the other flat branch 25 being applied against the corresponding branch of the other corner iron. The elements 23 are pierced transversely with a tapping into which there is screwed a screw 26 which allows the branches 24 to be locked in an adjustable position relative to the flexible tubes 6. In order to be able to regulate the spacing of these rods and to adapt it to the dimension of the foot of the patient, one of the branches 25 is pierced with a longitudinal cut-out, facing which the other branch 28 has a tapping, so as to be able to lock them in any position by means of at least one screw 27 (two in the present case). A sole 33 of a flexible material comprising, on its lower face, recesses 34 for the heads of screws 27, is engaged on the latter so that the patient can bear on this sole without being in direct contact with the screws.

In order to conform this apparatus to the limb to be fitted, with a view to subsequently producing in the workshop an orthesis adapted to this limb, splints 1 equipped with flexible tubes 6 of a length adapted to that of the limb are first chosen, and they are fixed by means of the screws 31 on an adapted articulation 2. Screws 32 make it possible to adjust the splints in flexion or in extension relative to the articulations. These splints are held by means of straps on the limb of the patient in the standing position, that is to say in the position of use of an orthesis, with the articulation 2 in the desired position.

The corner irons 20 are then fixed on the articulation by means of the screws 19, at the level of the patient's knee, and they are locked by means of the screws 22 at the spacing corresponding to the dimension of the knee.

The metallic strips 1 are then curved to the profile of the limb to be fitted, after having loosened the screws 7 which lock the flexible tubes in position.

The rods 10 are then adjusted to the desired height and they are locked in position by means of the screws 13, while they are made integral with the sheaths 12 by means of the screws 18.

Finally, the position of the branches 24 relative to the flexible tubes 6 is adjusted by means of the screws 26, and their spacing is regulated by means of the screws 27.

The apparatus thus adjusted permits subsequent production of the desired orthesis in the workshop, adapting it exactly to the dimensions and to the shape of the limb to be fitted.

I claim:

1. Apparatus for plotting the configuration of a lower limb of the human body, comprising first and second pairs of upper and lower longitudinal upright splints arranged laterally respectively on first and second opposite sides of the lower limb, with the upper and lower longitudinal upright splints of each pair of splints being mutually articulated by an orthesis articulation (2), with each splint comprising a deformable metal strip (1) adjoining a deformable flexible tube (6), engaged in an opening in each of a plurality of plates (5) fixed to said deformable metal strip and extending generally perpendicular to an outer face of the deformable metal strip relative to the lower limb of the patient, and each plate (5) being provided with locking means (7) for locking the flexible tube (6) in position relative to the plate (5), to make the deformable metal strip rigidly integral in any position with the deformable flexible tube, such that the splints (1) are deformable and can be applied tightly against the lower limb to match the profile of the lower limb, and a plurality of crosspieces forming braces (8, 10, 12) which transversely connect the splints (1) on opposite sides of the lower limb at various intervals, the crosspieces (8, 10, 12) connecting the splints having an adjustable transverse dimension to regulate the transverse spacing of the splints, wherein certain of the crosspieces comprise two first elements (8), each of which is respectively integral with one of the splints (1) on opposite sides of the lower limb and connected by the crosspiece, said first elements (8) projecting laterally in a manner substantially perpendicular to the respective splint on each side of the limb, and two second elements (9-10, 11-12) adjustable in position, respectively, relative to the first elements, with the second elements being mutually coupled transversely in an adjustable manner, relative to the splints (1), such that at least one of the second elements can be brought into contact with the limb and an assembly including the second elements can be adapted to the transverse spacing of the splints, including locking means (13, 18) for locking the second elements relative to one another in an assembled position and relative to the first elements.

2. The apparatus as claimed in claim 1, wherein the first elements comprise rods (8) integral with the splints (1), and the second elements (9-10, 11-12) are slidably mounted on the rods (8).

3. The apparatus as claimed in claim 2, wherein one of the second elements comprises a rod (10) directed transversely relative to the splints and mounted slidably in a sheath (12) of an associated second element.

4. The apparatus as claimed in claim 3, wherein the second element capable of contacting the lower limb of the patient comprises the rod (10), which bears on the limb by a movable plate (15) slidably and pivotably mounted relative to the rod (10) and provided with a second locking means (17) for locking said movable plate in position.

5. The apparatus as claimed in claim 4, wherein the articulations (2) of the upper and lower splints (1) of each of the first and second pairs are connected by a crosspiece of adjustable width forming a brace (20).

6. The apparatus as claimed in claim 5, wherein the crosspiece comprises two rigid corner irons coupled to the articulations (2), and a locking means (21, 22) for locking the corner irons relative to each other in any position.

7. The apparatus as claimed in claim 6, wherein a lower end of each of the lower splints to be positioned at a foot of the patient's lower limb comprises an adjustable means (24, 25) adjustable in position relative to a respective splint and adjustable in spacing relative to the adjustable means (24, 25) associated with another splint, and third locking means (26, 27) provided for locking the adjustable means (24, 25) relative to each other and also relative to the lower ends of the splints.

8. The apparatus as claimed in claim 7, wherein the adjustable means comprises, for each splint, a corner iron having a first corner branch mounted slidably (24) relative to a respective splint and having a perpendicular corner branch contacting a perpendicular corner branch (25) of another corner iron, with said locking means (26, 27) locking in position the corner irons relative to the splints and the perpendicular corner branches (25) relative to each other.

* * * * *

UNITED STATES PATENT AND TRADEMARK OFFICE
CERTIFICATE OF CORRECTION

PATENT NO. : 5,065,770          Page 1 of 2

DATED : November 19, 1991

INVENTOR(S) : Michel Palfray

It is certified that error appears in the above-identified patent and that said Letters Patent is hereby corrected as shown below:

On the Title Page, Section [54]: before "PARAPLEGIC" insert --A--.

On the Title Page, Section [57]: delete entire Abstract, and insert the following:

Apparatus for plotting the conformation of a lower limb of the human body, comprising two sets of two longitudinal uprights, or splints (1), articulated by an orthesis articulation (2), and a plurality of crosspieces forming braces (8, 10, 12) which transversely connect the splints (1) at various intervals. The splints (1) are deformable such that they can be applied tightly against the limb in order to match the profile thereof, and the crosspieces (8, 10, 12) connecting the splints have an adjustable transverse dimension, so as to be able to regulate the spacing of the splints.--

UNITED STATES PATENT AND TRADEMARK OFFICE
CERTIFICATE OF CORRECTION

PATENT NO. : 5,065,770
DATED : November 19, 1991
INVENTOR(S) : Michel Palfray

It is certified that error appears in the above-indentified patent and that said Letters Patent is hereby corrected as shown below:

Column 6, line 26, Claim 7: "adjustable in position" should read as --for adjusting the position of the lower splint--

Signed and Sealed this

Twenty-sixth Day of October, 1993

Attest:

BRUCE LEHMAN

Attesting Officer

Commissioner of Patents and Trademarks